US007806867B2

(12) United States Patent
Willis et al.

(10) Patent No.: US 7,806,867 B2
(45) Date of Patent: *Oct. 5, 2010

(54) INJECTION DEVICE

(75) Inventors: John P. Willis, Shirley, MA (US); Thaddeus G. Minior, Berlin, MA (US)

(73) Assignee: Valeritas, Inc., Parsippany, NJ (US)

(*) Notice: Subject to any disclaimer, the term of this patent is extended or adjusted under 35 U.S.C. 154(b) by 1178 days.

This patent is subject to a terminal disclaimer.

(21) Appl. No.: 10/658,116

(22) Filed: Sep. 8, 2003

(65) Prior Publication Data

US 2004/0220525 A1 Nov. 4, 2004

Related U.S. Application Data

(63) Continuation of application No. 09/755,906, filed on Jan. 5, 2001, now Pat. No. 6,616,627.

(60) Provisional application No. 60/174,876, filed on Jan. 7, 2000.

(51) Int. Cl.
*A61M 37/00* (2006.01)

(52) U.S. Cl. ........................................ 604/141; 604/69

(58) Field of Classification Search ................. 604/184, 604/226, 890.1, 68–72, 141, 143, 145–147, 604/140, 181, 187, 190, 218, 245; 222/251, 222/256, 260–261

See application file for complete search history.

(56) References Cited

U.S. PATENT DOCUMENTS

| | | | |
|---|---|---|---|
| 2,547,099 A | 4/1951 | Smoot | |
| 2,605,763 A | 8/1952 | Smoot | |
| 3,308,818 A | 3/1967 | Rutkowski | |
| 3,381,403 A | 5/1968 | Murdoch | |
| 3,387,609 A | 6/1968 | Shields | |
| 3,675,651 A | 7/1972 | Meyer | |
| 3,802,430 A | 4/1974 | Schwebel et al. | |
| 3,977,401 A | 8/1976 | Pike | |
| 3,977,402 A | 8/1976 | Pike | |
| 4,007,739 A | 2/1977 | Bron et al. | |
| 4,031,889 A * | 6/1977 | Pike | 604/144 |
| 4,059,107 A | 11/1977 | Iriguchi et al. | |
| 4,089,334 A | 5/1978 | Schewbel et al. | |
| 4,124,024 A | 11/1978 | Schewbel et al. | |
| 4,177,810 A | 12/1979 | Gourlandt | |
| 4,233,973 A | 11/1980 | Shukla | |
| 4,265,241 A | 5/1981 | Portner et al. | |

(Continued)

FOREIGN PATENT DOCUMENTS

EP 0 331 855 A2 9/1989

(Continued)

*Primary Examiner*—Theodore J Stigell
(74) *Attorney, Agent, or Firm*—Morgan, Lewis & Bockius LLP

(57) ABSTRACT

An injection device includes a housing having a proximal end and a distal end, the housing defining a distal opening, and a first opening in a side of the housing and between the proximal and distal ends; a propellant disposed inside the housing and spaced from the distal end; and a movable member disposed inside the housing and between the distal end and the propellant, wherein the propellant is in fluid communication with the movable member and the first opening.

14 Claims, 2 Drawing Sheets

U.S. PATENT DOCUMENTS

| | | | | | |
|---|---|---|---|---|---|
| 4,299,220 | A | | 11/1981 | Dorman | |
| 4,338,980 | A | | 7/1982 | Schwebel et al. | |
| 4,360,019 | A | | 11/1982 | Portner et al. | |
| 4,539,005 | A | | 9/1985 | Greenblatt | |
| 4,573,994 | A | | 3/1986 | Fischell et al. | |
| 4,596,556 | A | | 6/1986 | Morrow et al. | |
| 4,623,332 | A | * | 11/1986 | Lindmayer et al. | 604/68 |
| 4,626,244 | A | | 12/1986 | Reinicke | |
| 4,666,430 | A | | 5/1987 | Brown et al. | |
| 4,692,151 | A | | 9/1987 | Blackman | |
| 4,717,384 | A | | 1/1988 | Waldeisen | |
| 4,741,737 | A | | 5/1988 | Meyer et al. | |
| 4,773,900 | A | | 9/1988 | Cochran | |
| 4,790,824 | A | | 12/1988 | Morrow et al. | |
| 4,820,273 | A | | 4/1989 | Reinicke | |
| 4,828,548 | A | | 5/1989 | Walter | |
| 4,913,699 | A | | 4/1990 | Parsons | |
| 4,940,460 | A | | 7/1990 | Casey et al. | |
| 4,941,880 | A | | 7/1990 | Burns | |
| 4,955,871 | A | | 9/1990 | Thomas | |
| 4,966,581 | A | | 10/1990 | Landau | |
| 5,024,656 | A | | 6/1991 | Gassaway et al. | |
| 5,041,094 | A | | 8/1991 | Perego et al. | |
| 5,061,242 | A | | 10/1991 | Sampson | |
| 5,062,834 | A | | 11/1991 | Gross et al. | |
| 5,064,413 | A | * | 11/1991 | McKinnon et al. | 604/70 |
| 5,088,983 | A | | 2/1992 | Burke | |
| 5,147,311 | A | | 9/1992 | Pickhard | |
| 5,163,909 | A | | 11/1992 | Stewart | |
| 5,176,645 | A | | 1/1993 | Guerrero | |
| 5,179,022 | A | | 1/1993 | Sanford et al. | |
| 5,184,450 | A | | 2/1993 | Galy et al. | |
| 5,224,936 | A | | 7/1993 | Gallagher | |
| 5,304,128 | A | * | 4/1994 | Haber et al. | 604/68 |
| 5,308,335 | A | | 5/1994 | Ross et al. | |
| 5,312,335 | A | | 5/1994 | McKinnon et al. | |
| 5,312,577 | A | | 5/1994 | Peterson et al. | |
| 5,383,851 | A | | 1/1995 | McKinnon et al. | |
| 5,399,163 | A | | 3/1995 | Peterson et al. | |
| 5,466,220 | A | | 11/1995 | Brenneman | |
| 5,480,381 | A | | 1/1996 | Weston | |
| 5,492,534 | A | | 2/1996 | Athayde et al. | |
| 5,499,972 | A | | 3/1996 | Parsons | |
| 5,503,627 | A | | 4/1996 | McKinnon et al. | |
| 5,503,628 | A | | 4/1996 | Fetters et al. | |
| 5,520,639 | A | | 5/1996 | Peterson et al. | |
| 5,527,288 | A | | 6/1996 | Gross et al. | |
| 5,569,189 | A | | 10/1996 | Parsons | |
| 5,599,302 | A | | 2/1997 | Lilley et al. | |
| 5,607,418 | A | | 3/1997 | Arzbaecher | |
| 5,616,132 | A | | 4/1997 | Newman | |
| 5,618,269 | A | | 4/1997 | Jacobsen et al. | |
| 5,649,912 | A | | 7/1997 | Peterson | |
| 5,685,846 | A | | 11/1997 | Michaels, Jr. | |
| 5,693,017 | A | | 12/1997 | Spears et al. | |
| 5,704,911 | A | | 1/1998 | Parsons | |
| 5,730,723 | A | | 3/1998 | Castellano et al. | |
| 5,746,714 | A | | 5/1998 | Salo et al. | |
| 5,782,802 | A | | 7/1998 | Landlau | |
| 5,814,020 | A | | 9/1998 | Gross | |
| 5,836,915 | A | | 11/1998 | Steinbach et al. | |
| 5,846,233 | A | | 12/1998 | Lilley et al. | |
| 5,851,198 | A | | 12/1998 | Castellano et al. | |
| 5,858,001 | A | | 1/1999 | Tsals et al. | |
| 5,860,957 | A | | 1/1999 | Jacobsen et al. | |
| 5,891,085 | A | | 4/1999 | Lilley et al. | |
| 5,891,086 | A | * | 4/1999 | Weston | 604/70 |
| 5,893,397 | A | | 4/1999 | Peterson et al. | |
| 5,919,159 | A | | 7/1999 | Lilley et al. | |
| 5,936,514 | A | | 8/1999 | Anderson et al. | |
| 5,938,637 | A | | 8/1999 | Austin et al. | |
| 5,957,895 | A | | 9/1999 | Sage et al. | |
| 5,993,412 | A | | 11/1999 | Deily et al. | |
| 6,045,534 | A | * | 4/2000 | Jacobsen et al. | 604/156 |
| 6,056,724 | A | | 5/2000 | Lacroix | |
| 6,063,053 | A | | 5/2000 | Castellano et al. | |
| 6,074,360 | A | | 6/2000 | Haar et al. | |
| 6,096,002 | A | | 8/2000 | Landlau | |
| 6,099,504 | A | | 8/2000 | Gross et al. | |
| 6,132,395 | A | | 10/2000 | Landlau et al. | |
| 6,165,155 | A | * | 12/2000 | Jacobsen et al. | 604/156 |
| 6,258,062 | B1 | | 7/2001 | Thielen et al. | |
| 6,258,063 | B1 | | 7/2001 | Haar et al. | |
| 6,270,473 | B1 | | 8/2001 | Schwbel | |
| 6,319,224 | B1 | | 11/2001 | Stout et al. | |
| 6,406,455 | B1 | * | 6/2002 | Willis et al. | 604/68 |
| 6,592,545 | B1 | | 7/2003 | Bellhouse et al. | |
| 6,616,027 | B2 | | 9/2003 | Mochizuki | |
| 6,616,627 | B2 | * | 9/2003 | Willis et al. | 604/69 |
| 6,620,135 | B1 | * | 9/2003 | Weston et al. | 604/140 |
| 2001/0027290 | A1 | | 10/2001 | Weston | |
| 2001/0027293 | A1 | | 10/2001 | Joshi | |

FOREIGN PATENT DOCUMENTS

| | | | |
|---|---|---|---|
| EP | 0-427-457 | | 5/1991 |
| WO | WO-95/24176 | A1 | 9/1995 |
| WO | WO-98/31409 | | 7/1998 |
| WO | WO-99/21609 | A1 | 5/1999 |
| WO | WO-00/10630 | A1 | 3/2000 |
| WO | WO-00/48654 | A1 | 8/2000 |
| WO | WO-01/00346 | A1 | 1/2001 |
| WO | WO-01/05451 | A1 | 1/2001 |
| WO | WO-01/05452 | A1 | 1/2001 |
| WO | WO-01/13975 | A2 | 3/2001 |
| WO | WO-01/51109 | | 7/2001 |

* cited by examiner

INJECTION DEVICE

CROSS-REFERENCE TO RELATED APPLICATIONS

This application is a continuation of U.S. patent application Ser. No. 09/755,906, filed Jan. 5, 2001, now U.S. Pat. No. 6,616,627, issued Sep. 9, 2003, which claims priority under 35 USC §119(e)(1) to U.S. patent application Ser. No. 60/174,876, filed on Jan. 7, 2000, the entire contents of which are hereby incorporated by reference.

BACKGROUND

The invention relates to injection devices (e.g., injection devices including a needleless syringe), as well as components that can be used in injection devices.

Injection devices can be used for fluid injection into a body. Some injection devices can include a needleless syringe.

SUMMARY

The invention provides one or more components (e.g., a gas generant unit and/or a housing unit) that can be used in an injection device (e.g., an injection device including a needleless syringe), and injection devices containing one or more of these components.

The components can be removable, replaceable and/or adaptable to fit different sized injection devices. The injection devices can be re-usable. The injection devices can be in any of a variety of shapes and sizes.

For embodiments in which the injection device includes a gas generant unit, the gas generant unit can be removed before or after use of the injection device. Moreover, a gas generant unit that is removed from the syringe can be replaced with a different gas generant unit, which may contain the same or different gas generant compounds. Furthermore, a gas generant unit can be adaptable to fit different sized injection devices. Advantages associated with an injection device that is capable of using such a gas generant can include re-usability, relatively low cost to manufacture, relatively low cost to use, and/or enhanced flexibility in materials used as gas generant and/or injection fluid.

The injection device can include a housing that allows a fluid (e.g., a gas, such as a product of the reaction of the gas generant) to travel between the interior of the injection device and the exterior of the injection device without passing through the distal end of the injection device (e.g., the exit port of a syringe, such as a needleless syringe, contained within the injection device). In certain embodiments, this feature can be provided, for example, by including the following components in the housing: a sliding piston, a sleeve (which can have one or more venting mechanisms, such as one or more venting grooves, e.g., annular venting groove(s)), and one or more pressure relief mechanisms (e.g., one or more pressure relief holes). In these embodiments, the sliding piston can be designed to move along the sleeve so that, at one or more points along the path of motion of the sliding piston, the pressure relief mechanism(s) of the sliding piston align (e.g., partially align or fully align) with the pressure relief mechanism(s) in the sleeve. When this occurs, the fluid (e.g., reactant gas) can pass between the respective relief mechanism(s). The fluid (e.g., reactant gas) then exits the injection device via a passageway that does not include the distal end of the injection device (e.g., the exit port of a syringe, such as a needleless syringe, contained within the injection device).

In one aspect, the invention features an injection device, such as a needleless injection device, having a housing having a proximal end and a distal end, the housing defining a distal opening, and a first opening in a side of the housing and between the proximal and distal ends; a propellant disposed inside the housing and spaced from the distal end; and a movable member disposed inside the housing and between the distal end and the propellant, wherein the propellant is in fluid communication with the movable member and the first opening.

Embodiments include one or more of the following features.

The propellant is capable of forming a gas capable of moving the movable member in a distal direction and flowing through the first opening to the exterior of the housing.

The movable member comprises a piston defining a cavity, and the propellant is in fluid communication with the cavity. The movable member further defines a second opening in fluid communication with the first opening.

The device further includes a hollow sleeve configured to mate with the piston, the sleeve defining a second cavity in fluid communication with the propellant. The sleeve further defines a third opening alignable with the second opening. The sleeve further defines a groove, and the third opening is disposed in the groove.

The device further includes a button at the proximal end of the housing; a battery inside the housing and adjacent to the button; electrical leads in electrical communication with the battery; and a wire in electrical communication with the electrical leads, the wire configured to trigger the propellant.

The distal opening of the housing is configured to mate with a proximal end of a syringe. The syringe includes a plunger, and the movable member is configured to move the plunger in a distal direction.

The propellant includes a chemical pyrotechnic material.

The housing is composed of a plurality of detachable housings.

In another aspect, the invention features an injection device, such as a needleless injection device, having a housing having a proximal end and a distal end, the housing defining a distal opening, and a first opening in a side of the housing and between the proximal and distal ends; a propellant disposed inside the housing and spaced from the distal end; a sleeve disposed inside the housing and between the distal end and the propellant, the sleeve defining a second opening and a first cavity, the second opening and the first cavity in fluid communication with the propellant; and a piston mateable with the sleeve and movable in a distal direction, the piston defining a third opening alignable with the second opening, wherein the propellant is in fluid communication with the first opening when the second and third openings are aligned.

Embodiments include one or more of the following features.

The propellant is capable of forming a gas capable of flowing through the first cavity to move the piston, wherein the gas flows through the second and third openings when aligned, and through the first opening. The propellant includes a chemical pyrotechnic material.

The piston is coaxial with the sleeve and slidable over the sleeve to align the second and third openings. The piston defines a plurality of openings alignable with the second opening.

The sleeve defines a groove, such as an annular groove, the second opening disposed in the groove.

The distal opening of the housing is configured to mate with a syringe having a plunger, and the piston is configured to move the plunger.

The device further includes a button at the proximal end of the housing; a battery inside the housing and adjacent to the button; electrical leads in electrical communication with the battery; and a wire in electrical communication with the electrical leads, the wire configured to trigger the propellant.

The housing further defines an elongate passageway between the first opening and the third opening.

The device further includes a filter between the propellant and the first cavity.

The housing is composed of a plurality of detachable housings.

In another aspect, the invention features an apparatus that includes a housing, a button connected to the housing, a battery adjacent the button and connected to the housing, electrical leads in electrical communication with the battery, and a wire in electrical communication with the electrical leads.

In another aspect, the invention features an apparatus that includes a sleeve having a surface having at least one hole, a movable piston having at least one hole and a surface adjacent the surface of the sleeve, and a first housing connected to the sleeve and the movable piston.

In a further aspect, the invention features an injection device including first, second, third and fourth housings. The first housing is demountably attached to the second housing. The second housing is demountably attached to the third housing. The third housing is demountably attached to the fourth housing. The first housing includes a button and a battery adjacent the button. The second housing includes an inner housing, electrical contacts within the inner housing, a wire within the inner housing and in electrical communication with the electrical contacts, and a gas generant within the inner housing. The third housing includes a syringe adaptor housing having an outer vent sleeve, a movable piston having an end and at least one relief hole, a fixed sleeve having a groove with a hole (e.g., a pressure relief hole), the fixed sleeve being adjacent the movable piston, a drive piston having at least one groove, the drive piston being adjacent the end of the movable piston and a sealing device within the groove of the drive piston. The fourth housing includes a plunger having an end, a syringe adjacent the end of the plunger, and an elastomeric spring adjacent the syringe.

Other features, objects, and advantages of the invention will be apparent from the description and drawings, and from the claims.

DETAILED DESCRIPTION

The invention relates to injection devices (e.g., injection devices containing needleless syringes) and components that can be used in such injection devices. Advantages of the injection devices can include that they are relatively safe to use, relatively less painful to use, capable of delivering fluid in a predetermined and/or desirable manner, and/or reusable.

Figure 1:
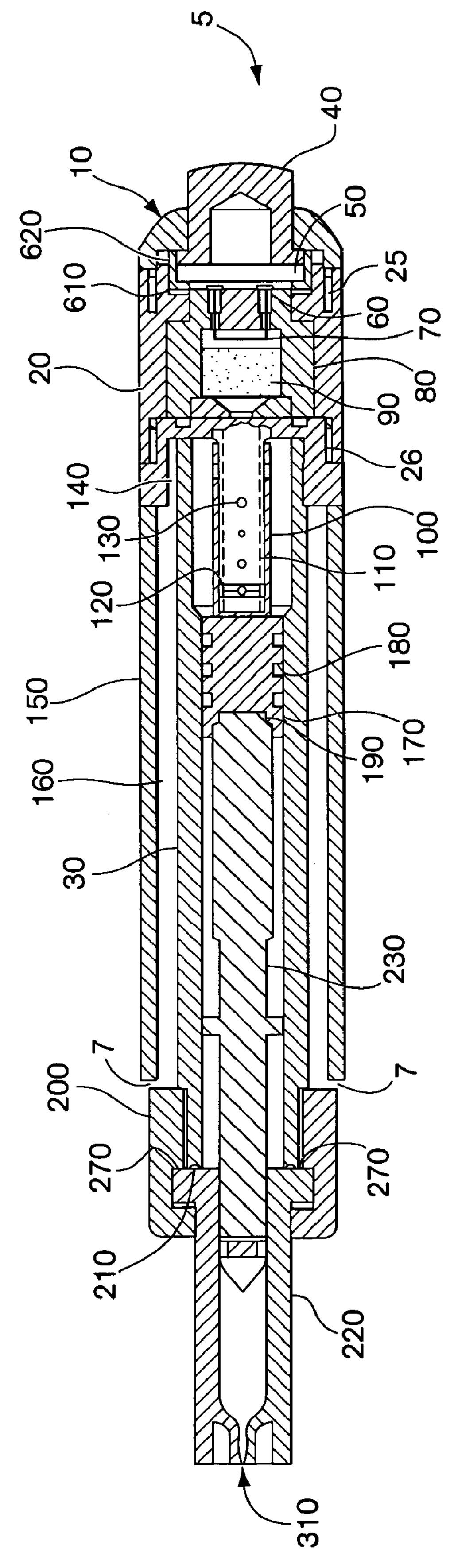
FIG. 1 is a cross-sectional view of an embodiment of an injection device.

FIG. 1 shows a cross-sectional view of an embodiment of an injection device 5. Device 5 includes housings 10, 20, and 30. Housing 10 is demountably attached to housing 20 at section 25 by for example, screw threads or a bayonet lock. Housing 20 is demountably attached to housing 30 at section 26 by, for example, screw threads or a bayonet lock. Housing 30 is permanently attached to a bayonet interlock syringe adaptor 200 to provide a mechanism for fitting a syringe configuration.

Figure 3:
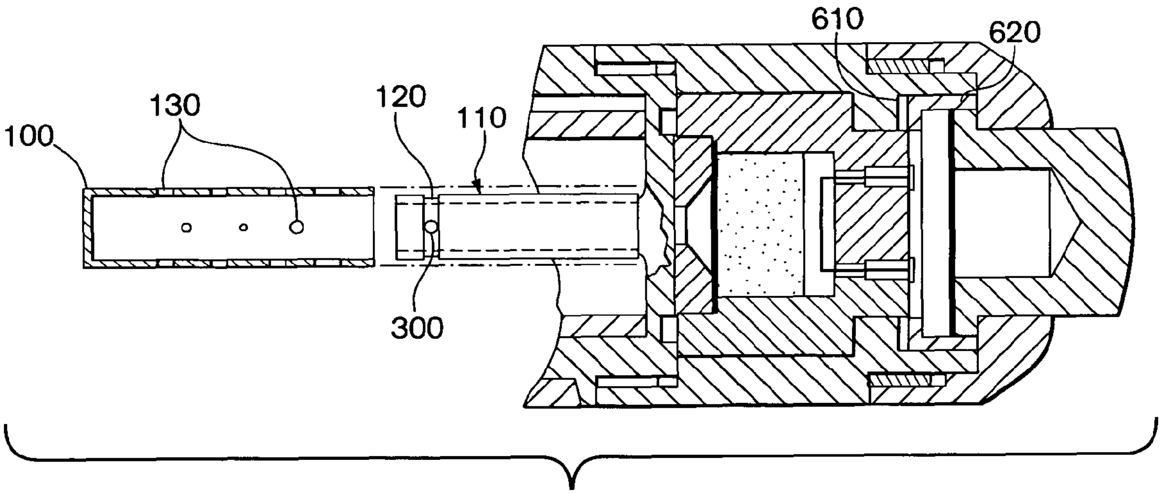
FIG. 3 is a partial cross-sectional view of an embodiment of a portion of an injection device.

Housing 10 includes a button 40, a battery 50, and an electrically insulative (e.g., non-metallic) cup 620 (FIG. 3).

Figure 2:
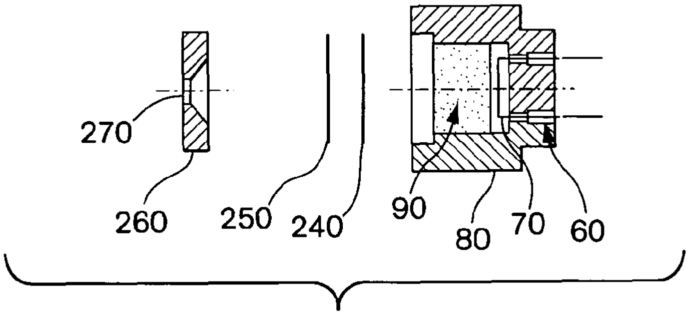
FIG. 2 is a partial cross-sectional view of an embodiment of a portion of an injection device.

Housing 20 encloses a housing 80 (e.g., a disposable housing) having electrical contacts 60, a wire 70 and a propellant 90, such as a gas generant (FIG. 2).

The syringe adaptor 200 has an outer vent sleeve 150, a sliding piston 100 having pressure relief holes 130, sleeve 10 (e.g., a fixed sleeve) having a groove 120 (e.g., an annular groove), and a drive piston 170 having grooves containing sealing devices 180 (e.g., o-rings) and a syringe interface 190 (e.g., a custom syringe interface) located at its distal end. The sliding piston 100 includes a proximal end toward the proximal end of the housing and a distal end toward the distal end of the housing. The sleeve 110 includes a proximal end toward the proximal end of the housing and a distal end toward the distal end of the housing.

In some embodiments, the injection device 5 is assembled as follows. Sleeve 110 is permanently attached to housing 30, followed by permanently attached outer vent sleeve 150 to the flange of sleeve 110. Then, elastomeric spring 210 is bonded to the end of housing 30, and syringe adaptor 200 is subsequently permanently attached to housing 30.

Syringe adaptor 200 (e.g., an interlock adaptor) accepts a syringe housing 220 with its associated plunger 230.

FIG. 2 shows an exploded view of an embodiment of housing 80 including electrical contacts 60, wire 70, propellant 90, screen 240, filter 250 and cap 260 with an exit hole 270.

FIG. 3 shows an exploded view of an embodiment of sleeve 110, annular groove 120 having hole(s) 300, sliding piston 100 and vent holes 130.

During operation of injection device 5, button 40 (e.g., a molded plastic button) is pressed, compressing a wave spring 610 which causes battery 50 (e.g., a replaceable battery) to come into contact with electrical contacts 60. This causes an electrical current to pass through wire 70 (e.g., a metal wire such as nickel/chromium wire, and/or a wire having a diameter of from about 0.005 inch to about 0.010 inch, such as about 0.010 inch), thereby heating wire 70 (e.g., causing wire 70 to become red hot in about one second). The heat generated by wire 70 is sufficient to cause the reaction of chemical components contained in propellant 90. Such chemical components can include a fuel and an oxidant. A nonlimiting, illustrative list of examples of chemical components that can be used in propellant 90 (e.g., a gas generant) are disclosed in U.S. Pat. Nos. 4,103,684; 4,342,310; 4,447,225; 4,518,385; 4,592,742; 4,623,332; 4,680,027; 4,722,728; 4,913,699; 5,024,656; 5,049,125; 5,064,123; 5,190,523; 5,304,128; 5,312,335; 5,334,144; 5,383,851; 5,399,163; 5,499,972; 5,501,666; 5,503,628; 5,520,639; 5,569,189; 5,630,796; 5,704,911; 5,730,723; 5,840,061; 5,851,198; 5,879,327; 5,899,879; 5,899,880; 5,911,703; and 5,993,412, each of which is hereby incorporated by reference. Other chemical components are described in commonly-assigned Application No. 60/250,573, filed Nov. 30, 2000, and entitled "Injection Devices", hereby incorporated by reference.

The gas formed by the reaction of the chemical components in propellant 90 passes through screen 240 (e.g., metal screen, such as a stainless steel screen of, for example, about 50 to 200 mesh) and filter 250 (e.g., a glass fiber filter). Screen 240 can cool the reactant gas and/or trap slag, and filter 250 can trap particulates (e.g., small particulates, such as those generated during the reaction).

After passing through filter 250, the reactant gases cause sliding piston 100 to move along the surface of sleeve 110. As piston 100 moves along the surface of sleeve 110, piston 100 urges drive piston 170 to push against plunger 230 which, in turn, pushes against fluid within syringe 220, thereby ejecting fluid from syringe 220 via outlet 310.

The movement of piston 100 along the surface of sleeve 110 also causes holes 130 to reach the annular groove 120. When this occurs, the reactant gas can pass through one or more holes 300 (i.e., one, two, three or four holes) in the annular groove 120 and one or more of holes 130. The reactant gas that passes through holes 300 and hole(s) 130 can flow through relief channels 140, into space 160 (e.g., an open space, or a space containing a filter material, such as glass wool) and out device 5 via gas vent 7.

The number, size and location of holes 130 can vary to assist in controlling the pressure of fluid exiting through distal end 310 of injection device 5. The location of holes 130 can be determined by interfacing the end of the syringe to a pressure transducer that in turn is interfaced to a real time data acquisition system. One example is a model PCI-731/6040E data acquisition board (commercially available from National Instruments of Austin, Tex.), which can be interfaced to a computer (e.g., a personal computer) for real time pressure transducer measurements. Changes in the pressure profile due to changes in the placement, shape, and size of holes 130 can be monitored and optimized accordingly.

The use of annular groove 120 can obviate the need for a precise alignment of holes 130 because holes 130 are not required to be keyed to contact groove 120.

Syringe 220 and plunger 230 can take on a variety of shapes and sizes. For example, syringe 220 and plunger 230 can be commercially available components (e.g., such as available from Bioject Medical, located in Portland, Oreg.; Injet Medical Products, Inc., located in Lake Forest, Ill.; and Avant Drug Delivery Systems, Inc., located in San Diego, Calif.).

The end of housing 30, syringe adaptor 200 and elastomeric spring 210 form an interlock, which, in certain embodiments, can be designed to accept the attachment of commercially available syringes and/or ampules. The interlock may be one of several types including a bayonet type.

In certain embodiments, housing 80 is replaceable. In these embodiments, after an injection housing 80 can be removed and replaced with a different housing, and device 5 can be re-used.

The invention is not limited by the above description, and the invention contemplates variations and modifications to this description. For example, in some embodiments, housings 10, 20, and 30 can be non-demountable.

In some embodiments, the invention provides for the delivery of a mixture of two substances.

The first substance can be a dry substance, e.g., a lyophilized protein, nucleic acid, e.g., RNA or DNA, or polysaccharide. The first substance can be a vaccine, or a drug. The first substance can be a peptide, polypeptide, or protein, e.g., an antibody, an enzyme, a hormone or growth factor. Preferred first substances include insulin. The first substance can be: a blood protein, e.g., clotting factor VIII or a IX, complement factor or component; a hormone, e.g., insulin, growth hormone, thyroid hormone, a catecholamine, a gonadotrophin, PMSG, a trophic hormone, prolactin, oxytocin, dopamine and the like; a growth factor, e.g., EGF, PDGF, NGF, IGF's and the like; a cytokine, e.g., an, interleukin, CSF, GMCSF, TNF, TGF-alpha, TGF-beta. and the 25 like; an enzyme, e.g., tissue plasminogen activator, streptokinase, cholesterol biosynthetic or degradative, glycosolases, and the like; a binding protein, e.g., a steroid binding protein, a growth hormone or growth factor binding protein and the like; an immune system protein, e.g., an antibody, SLA or MHC gene or gene product; an antigen, e.g., a bacterial, parasitic, or viral, substance or generally allergens and the like.

The second substance can be a liquid, e.g., a diluent or solute. Such liquids can include buffers, inert fillers, pharmaceutically acceptable carriers, or the like.

The subject can be a human or an animal, e.g., a laboratory animal, or pet, e.g., a dog or cat, or other animal, e.g., a bovine, a swine, a goat, or a horse. The first and second substance can be combined by the subject, or by another person.

Other embodiments are in the claims.

What is claimed is:

1. An injection device for fluid injection into a body comprising:

a housing having a proximal end and a distal end, the housing having an opening proximate the distal end, the opening configured to deliver a fluid;

a fluid chamber disposed inside the housing and configured to contain the fluid;

a propellant chamber disposed inside the housing and spaced from the distal end of the housing;

a sleeve having a proximal end and a distal end, the sleeve disposed inside the housing between the distal end of the housing and the propellant chamber, the sleeve having a first cavity in fluid communication with the propellant chamber, and having an opening between the proximal end of the sleeve and the distal end of the sleeve; and a piston mounted on the sleeve and having a proximal end and a distal end and having an opening between the proximal end of the piston and the distal end of the piston, the piston being coupled to the sleeve and having a second cavity, the piston being movable with respect to the sleeve from a first position to a second position, wherein, during use, a fluid is released from the propellant chamber causing the piston to slide over a surface of the sleeve from the first position to the second position, movement of the piston causing the fluid in the fluid chamber to be ejected through the housing opening, and wherein as the piston slides over the sleeve, the opening of the piston aligns with the opening of sleeve such that at least some of the fluid from the propellant chamber travels through the aligned openings of the sleeve and piston.

2. The injection device of claim 1, wherein the opening of the piston is configured to assist in controlling pressure of the fluid being ejected through the housing opening.

3. The injection device of claim 1, wherein the sleeve further includes a groove, the opening of the sleeve disposed in the groove.

4. The injection device of claim 3, wherein the groove is annular.

5. The injection device of claim 1, wherein the opening of the piston includes a plurality of axially spaced openings that are each alignable with the opening of the sleeve.

6. The injection device of claim 1, wherein the housing is comprised of a plurality of housing components.

7. The injection device of claim 1, wherein the fluid from the propellant chamber is a gas that urges the piston from the first position to the second position.

8. The injection device of claim 1, wherein the second cavity is in fluid communication with an exterior of the housing when the piston and sleeve openings are aligned.

9. The injection device of claim 1, wherein the fluid from the propellant chamber is released from a propellant disposed within the propellant chamber.

10. The injection device of claim 9, further comprising:

a button coupled to the housing proximate the proximal end of the housing;

a battery disposed inside the housing and adjacent to the button;

electrical leads in electrical communication with the battery; and a wire in electrical communication with the electrical leads, the wire configured to trigger the propellant.

11. The injection device of claim 9, wherein the propellant includes a chemical pyrotechnic material.

12. The injection device of claim 1, wherein the device is a needleless injection device.

13. The injection device of claim 1, further comprising:

a filter disposed between the propellant chamber and the first cavity.

14. The injection device of claim 1, wherein the housing includes a vent, at least some of the fluid from the propellant chamber exiting through the vent after traveling through the openings of the sleeve and the piston.

* * * * *